US00PP18342P2

(12) United States Plant Patent
Whetman

(10) Patent No.: US PP18,342 P2
(45) Date of Patent: Dec. 25, 2007

(54) ***DIANTHUS* PLANT NAMED 'CRANBERRY ICE'**

(50) Latin Name: *Dianthus×hybrida*
Varietal Denomination: Cranberry Ice

(76) Inventor: John Whetman, Deer Park Farm, Chudleigh, Newton Abbot Devon (GB), TQ130NH ( * ) Notice: Subject to any disclaimer, the term of this patent is extended or adjusted under 35 U.S.C. 154(b) by 170 days.

(21) Appl. No.: 11/325,479

(22) Filed: Jan. 3, 2006

(51) Int. Cl.
*A01H 5/00* (2006.01)

(52) U.S. Cl. ..... Plt./281
(58) Field of Classification Search ..... Plt./281
See application file for complete search history.

*Primary Examiner*—Wendy C. Haas
*Assistant Examiner*—Georgia Helmer

(57) ABSTRACT

A new cultivar of *Dianthus* plant named 'Cranberry Ice' that is characterized by pronounced compact habit, grey-green foliage, and vivid magenta flowers. In combination these traits set 'Cranberry Ice' apart from all other existing varieties of *Dianthus* known to the inventor.

2 Drawing Sheets

Genus: *Dianthus.*
Species: ×*hybrida.*
Denomination: 'Cranberry Ice'.

BACKGROUND OF THE INVENTION

The present invention relates to a new and distinct cultivar of carnation that is grown for use as a flowering plant for pots and containers. The new cultivar is known botanically as *Dianthus×hybrida* and will be referred to hereinafter by the cultivar name 'Cranberry Ice'.

'Cranberry Ice' is a complex hybrid plant that is the product of a breeding program started by the inventor in 1985. The breeding program is ongoing, conducted in a cultivated area of Houndspool, Dawlish, Devon, United Kingdom. The primary focus of the breeding program is to produce new cultivars of carnations that exhibit unique growth habit. The inventor selected 'Cranberry Ice' in 2001 for its unique pronounced compact habit accompanied by abundant vivid magenta flowers that bloom from May through October.

'Cranberry Ice' is a dwarf carnation exhibiting pronounced compact habit, grey-green foliage, and vivid magenta flowers. The surfaces of stems, leaves, calyx, and epicalyx all exhibit the characteristic waxy bloom of *Dianthus.* 'Cranberry Ice' is a complex hybrid plant that resulted from the open pollination between large families of seedlings from *Dianthus* 'Queen of Henri' (unpatented) and *Dianthus* 'Waithman's Beauty' (unpatented). The variety of *Dianthus* which is considered by the inventor to most closely resemble 'Cranberry Ice' is the inventor's variety *Dianthus* 'Spangled Star' (U.S. Plant Pat. No. 13,029). When compared to 'Spangled Star', 'Cranberry Ice' is more vigorous with larger flowers. 'Cranberry Ice' has a longer flowering period than 'Spangled Star'. The flowers of 'Cranberry Ice' are more purple in color than 'Spangled Star'.

Asexual reproduction of the new cultivar was first accomplished by the inventor in 2001 in a cultivated area of Houndspool, United Kingdom. The method of asexual propagation used was vegetative cuttings. Since that time the characteristics of the new cultivar have been determined stable and are reproduced true to type in successive generations of asexual reproduction.

SUMMARY OF THE INVENTION

The following traits have been repeatedly observed and represent the characteristics of the new *Dianthus* cultivar 'Cranberry Ice'. These traits in combination distinguish this cultivar from all other commercial varieties known to the inventor. 'Cranberry Ice' has not been tested under all possible conditions and phenotypic differences may be observed with variations in environmental, climatic and cultural conditions, however, without any variance in genotype.

1. *Dianthus* 'Cranberry Ice' exhibits a pronounced compact habit.
2. *Dianthus* 'Cranberry Ice' blooms profusely.
3. *Dianthus* 'Cranberry Ice' exhibits vivid magenta flowers from May through October.
4. *Dianthus* 'Cranberry Ice' exhibits grey-green foliage.
5. At maturity, the height of the foliage mound of *Dianthus* 'Cranberry Ice' is 20 cm to 25 cm. The mature width is 25 cm to 35 cm.
6. *Dianthus* 'Cranberry Ice' is an herbaceous perennial.
7. *Dianthus* 'Cranberry Ice' is suitable for use as a flowering plant in pots, containers, window boxes and the garden.
8. *Dianthus* 'Cranberry Ice' is hardy to minus 15° Centigrade.

BRIEF DESCRIPTION OF THE DRAWINGS

The accompanying color drawings illustrate the overall appearance of the new *Dianthus* variety 'Cranberry Ice' showing colors as true as it is reasonably possible to obtain in colored reproductions of this type. Colors in the drawings may differ from the color values cited in the detailed botanical description, which accurately describe the actual colors of the new variety 'Cranberry Ice'.

The drawing labeled as FIG. 1 depicts an entire plant.

Figure 2:
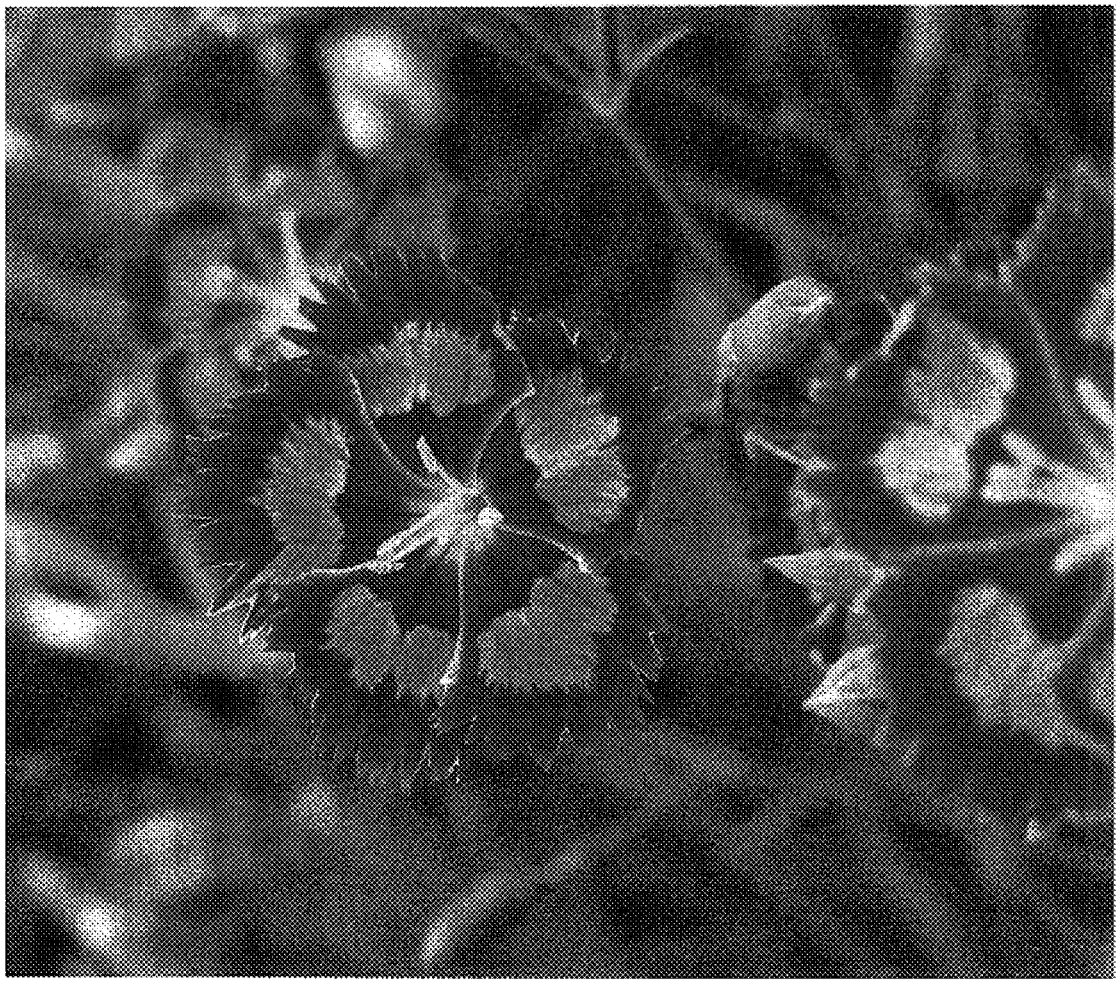

The drawing labeled as FIG. 2 is a close-up of flowers.

Figure 1:
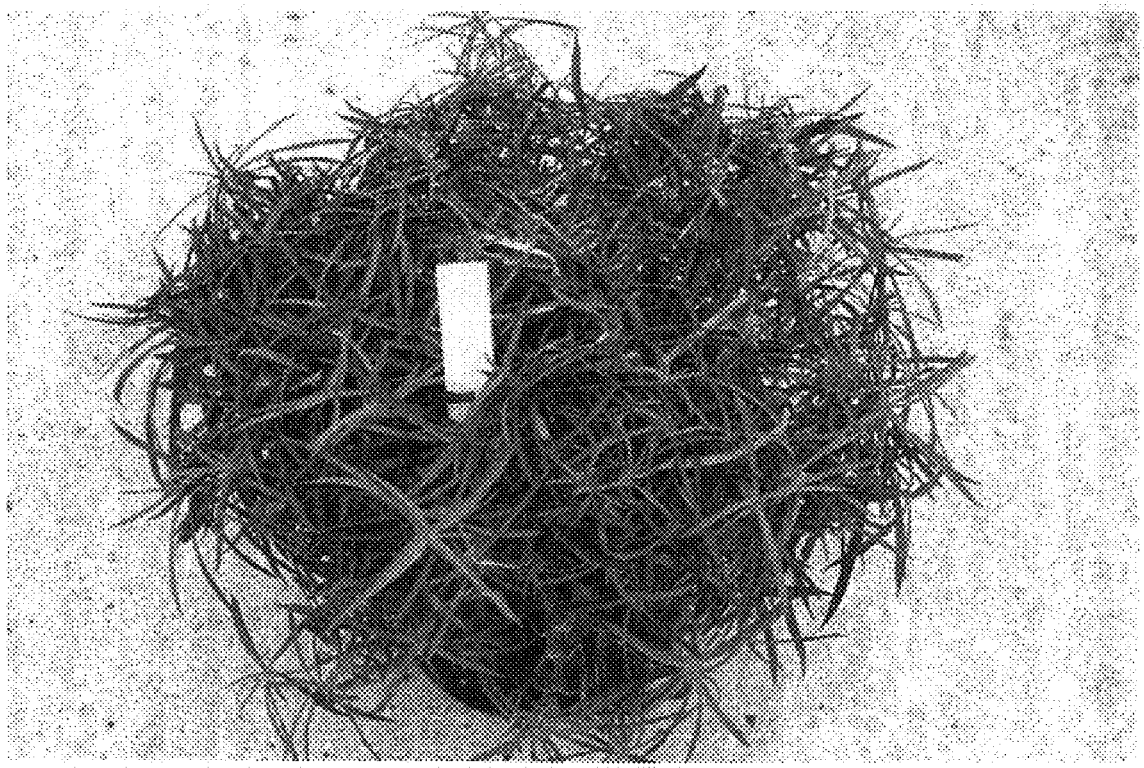

FIG. 1 was made of a plant grown in a 3 liter container and FIG. 2 was made of a plant grown in 1.5-liter container in a cold glasshouse in Devon, United Kingdom. No chemicals were used to treat the plant. The drawings were made using conventional techniques and although colors may appear different from actual colors due to light reflectance they are as accurate as possible by conventional photography.

The age of the plant in FIG. 1 is 4–6 months of age, and in FIG. 2 is 9 months of age.

BOTANICAL DESCRIPTION OF THE PLANT

The following is a detailed description of the new cultivar 'Cranberry Ice'. Data was collected in spring from 1.5-liter container plants in spring, and grown indoors in Devon, United Kingdom. The color determinations are in accordance with the 2001 edition of The Royal Horticultural Society Colour Chart except where general color terms of ordinary dictionary significance are used. No chemicals were used to treat the plants. Growing conditions are typical to other *Dianthus*.

Botanical classification: *Dianthus* 'Cranberry Ice'.
Species: ×*hybrida*.
Common name: Dwarf carnation.
Commercial classification: *Dianthus* hybrid.
Type: Perennial herb.
Use: Used as a flowering plant for pots, containers and the garden.
Parentage: 'Cranberry Ice' is a complex hybrid plant that resulted from the open pollination between large families of seedlings from *Dianthus* 'Queen of Henri' (unpatented) and *Dianthus* 'Waithman's Beauty' (unpatented).
Plant description:
- *Bloom period.*—May through October.
- *Plant habit.*—Compact, mounding.
- *Plant height.*—20 cm–25 cm in height at maturity.
- *Plant width.*—25 cm–35 cm in width at maturity.
- *Plant hardiness.*—Hardy to minus 15° Centigrade.
- *Root system.*—Fine fibrous roots.
- *Propagation.*—Propagation is accomplished using vegetative cuttings.
- *Cultural requirements.*—Grow in full sun in well-drained, moderately fertile soil.
- *Diseases and pest.*—Susceptible to known *Dianthus* pests and disease but no other susceptibilities to pests or disease are known to the inventor.
- *Time and temperature needed to produce a rooted cutting.*—3 weeks are needed to produce roots on cuttings using a mist propagation unit with bottom heat of 21° Centigrade, and a minimum air temperature of 15° Centigrade.
- *Crop time.*—An average of 3 months in the spring and 6 months in the fall is needed to produce a finished container size plant from a well-rooted cutting.

Stem:
- *Shape.*—Cylindrical.
- *Stem dimensions.*—150 mm in length, and 3 mm in diameter.
- *Stem surface.*—Glabrous and glaucous.
- *Stem color.*—135B.
- *Branching.*—Numerous branching shoots from the axils of lower leaves.
- *Internode length.*—10 mm to 20 mm. between nodes.
- *Node color.*—145C.
- *Node dimensions.*—4 mm in diameter and 3 mm in length.

Foliage:
- *Type.*—Evergreen.
- *Shape.*—Linear.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement.*—Opposite and spiraling up stem.
- *Surfaces* (*adaxial and abaxial*).—Glaucous.
- *Leaf dimensions.*—110 mm in length and an average of 5 mm in width.
- *Leaf color* (*adaxial and abaxial surfaces*).—N133A.
- *Fragrance.*—Absent.

Flowers:
- *Inflorescence.*—Cymose.
- *Flower type.*—Salviform, double and symmetrical.
- *Flower dimensions* (*including calyx*).—30 mm in length and 40 in diameter.
- *Fragrance.*—Slightly clove-like.
- *Bud.*—Shape: Ovoid, cylindrical. Dimensions: 15 mm–18 mm in length, 8 mm–10 mm in diameter. Color: N138C. Anthocyanin: Absent.
- *Petals.*—Persistent, single, apopetalous, slightly overlapping. Number: Five petals. Margin: Crenate-dentate (toothed 2 mm deep). Shape: Obteltoid and slightly folded. Surface: Glabrous. Dimensions: 45 mm. in length and 20 mm. in width. Color pattern: Crimson blade with pink patch across center. Upper surface: Ground color of blade: 73A. Color of band around center: 64A. Color of middle of strap: 145B. Color of base of strap: 145D. Lower surface: Ground color of blade: 75B. Color of band around center: none. Color of middle of strap: 145B. Color of base of strap: 145D.
- *Calyx.*—Shape: Cylindrical. Dimensions: 8 mm in diameter and 20 mm in length. Anthocynanin: Absent. Sepals: Five in number. Fused or unfused: Sepals fused. Color: 133B. Anthocyanin: Present on sepal margins which appear tinged 58A.
- *Peduncle dimensions.*—150 mm in length and 2 mm in diameter.
- *Peduncle color.*—N138C.
- *Peduncle surface.*—Glaucous.
- *Epicalyx.*—Present, 2 pairs of opposite bracts.
- *Bracts* (*longer pair*).—Dimensions: 5 mm in width and 8 mm in length. Color: 133B. Anthocyanin: Absent.
- *Bracts* (*shorter pair*).—Dimensions: 3 mm in width, 5 mm in length. Color: 133B. Anthocyanin: Absent.
- *Lastingness of flower.*—Each individual flower lasts an average of 10 days on or off the plant at 20° centigrade.

Reproductive organs:
- *Stamens.*—Number: 10. Dimensions: 30 mm in length and 1 mm in diameter. Color: 73D.
- *Anther.*—Number: 10. Dimensions: 2 mm in length and 1 mm in diameter. Color: 73D. Attachment: Dorsi-fixed.
- *Pollen.*—Present.
- *Pollen color.*—190B.
- *Pistil.*—One that divides into two above the ovary.
- *Pistil dimensions.*—37 mm. in length, 1 mm in diameter.
- *Styles.*—Number: 2. Dimensions: 35 mm in length and 1 mm in width. Color: 73D.
- *Stigma.*—Color: 73D. Height above petals: 15 mm above petals.
- *Ovary.*—Position: Superior. Dimensions: 15 mm in length and 4 mm in diameter. Shape: Spindle shaped. Color: Upper 144B, lower 144D.

Seed:

*Seed.*—Present.

*Dimensions.*—2 mm in length, 1 mm in width.

*Shape.*—Flattened and wrinkled.

*Color.*—Black.

What is claimed is:

1. A new and distinct cultivar of *Dianthus* plant named 'Cranberry Ice' as described and illustrated herein.

* * * * *